US00PP13322P2

(12) United States Plant Patent
Häussermann

(10) Patent No.: US PP13,322 P2
(45) Date of Patent: Dec. 3, 2002

(54) VARIETY OF SALVIA PLANT NAMED 'HAEUMANARC'

(75) Inventor: Martin Häussermann, Möglingen (DE)

(73) Assignee: Haussermann Stauden & Geholze GBR (DE)

( * ) Notice: Subject to any disclaimer, the term of this patent is extended or adjusted under 35 U.S.C. 154(b) by 0 days.

(21) Appl. No.: 10/074,613

(22) Filed: Feb. 13, 2002

(51) Int. Cl.[7] ..... A01H 5/00
(52) U.S. Cl. ..... Plt./263
(58) Field of Search ..... Plt./263, 226

(56) References Cited

U.S. PATENT DOCUMENTS

PP10,316 P * 4/1998 Dorman ..... Plt./263

OTHER PUBLICATIONS

UPOV ROM GTITM Computer Database, GTI JOUVE Retreival Software, citation(s) for 'Haeumanarc'.*

* cited by examiner

*Primary Examiner*—Bruce R. Campell
*Assistant Examiner*—W C Baker
(74) *Attorney, Agent, or Firm*—Webb Ziesenheim Logsdon Orkin & Hanson, P.C.

(57) ABSTRACT

A new and distinct early flowering Salvia plant with deep violet colored flowers and dwarf growth habit suitable for potting.

1 Drawing Sheet

BOTANICAL CLASSIFICATION

*Salvia nemorosa L.*

BACKGROUND OF THE INVENTION

The present invention comprises a new and distinct cultivar of *Salvia nemorosa L.* plant known by the varietal name 'Haeumanarc'. The new variety was discovered as a naturally occurring mutation of 'Ostfriesland' (unpatented) in a bed of sage plants in Stuttgart, Germany in the summer of 1998. The new variety is smaller than its parent at 20–30 cm high compared to typical height of about 40 cm for *Salvia nemorosa L.* and has deeper violet colored flowers than its parent. The growth rate is slower for the new variety at about 8 cm per month compared to about 10–12 cm per month for its parent. The lateral branches length of 20 cm and inflorescence height of 7 cm of the new variety are less than those of the parent at about 30 cm and over 15 cm, respectively. The new variety was first asexually reproduced in 1999 by cuttings in Stuttgart, Germany. The new variety has been trial and field tested at Stuttgart and has been found to retain its distinctive characteristics and remain true to type through successive propagations.

The following traits in combination distinguish 'Haeumanarc' as a new and distinct cultivar:

1. Dwarf growth making it useful as a potted plant or for borders in gardens.

2. Deep violet flower color.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth characteristics of the new cultivar. The data which defines these characteristics were collected by asexual reproductions carried out in Stuttgart, Germany. Plants for the description were 2 years old, grown in fields and in 9 cm and 11 cm pots in the spring and summer in Stuttgart, Germany at 14–27° C. daytime temperature and at 7–14° C. night temperature with normal outdoor light levels. The color readings were taken on a plant outdoors and in a greenhouse under natural light. Color references are primarily to The R.H.S. Colour Chart of The Royal Horticultural Society of London.

PLANT

Classification:
- *Botanical.*—*Salvia nemorosa L.*
- *Commercial.*—Sage.

Form: Globular shape.
Height: 2–5 cm from soil to top of flowers; 2.5 cm wide.
Growth: Herbaceous perennial, broad upright, about 8 cm growth per month in spring, moderate vigor.
Roots:
- *Habit.*—Fine, compact, dense, freely branching, white.
- *Time to initiate roots.*—About 20 days at 20° C.
- *Time to produce a rooted cutting.*—About 35 days at 20° C.

Stem:
- *Form.*—Quadrangular, strong.
- *Color.*—Dull, Green Group 138A.
- *Pubescence.*—Densely covered with short grayish white hairs, about 0.2 mm long.

Branching:
- *Form.*—Very free branching from base, no pinching required.
- *Diameter.*—3.5 mm.
- *Length.*—20 cm.
- *Internode length.*—1.2 cm.
- *Quantity.*—About 12 flowering lateral branches.

Foliage:
*Arrangement.*—Opposite.
*Number of leaves per branch.*—10 (5 pairs).
*Size of leaf.*—Length: 6 cm on average, shorter at tops of stems. Width: 2 cm.
*Shape of leaf.*—Lanceolate.
*Shape of tip.*—Acute.
*Shape of base.*—Rounded to slightly attenuate.
*Texture.*—Rugose.
*Pubescence.*—Very dense rugose hairs, light grayish-white, less than 0.1 mm long on underside of main vein.
*Margin type.*—Crenate.
*Color.*—Young leaves: Upper surface: Between Green Groups 137A and 141A. Lower surface: Green Group 137C. Mature leaves: Upper surface: Green Group 137A. Lower surface: Green Group 138A.
*Petioles.*—Length: 3.5 cm on average for lower leaves; 1.8 cm on average for other leaves. Diameter: 2 mm. Color: Green Group 138A.
*Veins.*—Pattern: Pinnate. Color: Upper surface: Green Group 138A. Lower surface: Green Group 138A.

Durability: Highly durable to stresses; when crushed, foliage spreads typical sage odor.

Response time to flower: About 10 months when grown in the field.

FLOWER

Natural flowering season: Continuous from July through September.

Inflorescence type and habit: Branched, terminal verticillaster, labiate, no fragrance, flower lasts about 6 days on plant, self-cleaning.

Rate of flower opening: About 25% of flowers open at once, all flowers open in about 4 weeks.

Number of flowers: About 75 per spike; about 350 buds and flowers per lateral branch; about 4,000 flowers per plant.

Inflorescence size:
*Diameter.*—2 cm.
*Height.*—7 cm.

Peduncle:
*Length.*—2.5 cm with secondary peduncles 1.6 cm long.
*Diameter.*—1.75 mm.
*Color.*—Between Green Group 138A and Green Group 138B.
*Orientation.*—Upright with secondary peduncles at 30–45°.
*Strength.*—Strong.

Corolla:
*Petal arrangement.*—Labiate with one upper lip and one 3-lobed lower lip having one main lobe and two smaller side lobes.
*Size.*—7 mm high; 4 mm wide.
*Margin.*—Entire upper lip; 3-lobed lower lip.
*Tip shape.*—Emarginate upper lip; rounded lower lip.
*Length.*—Average upper lip: 9 mm; average lower lip: 6 mm.
*Width.*—Average upper lip: 1 mm; average lower lip: 4 mm.
*Petal quantity.*—2, fused at base.
*Petal apex shape.*—Upper lip; broad elliptic; folded; lower lip spathulate.
*Texture.*—Numerous bristly glandular hairs on outside of upper lip, same color as upper lip, less than 0.1 mm long.
*Aspect.*—Drooping.
*Petaloids.*—None.

Color:
*Petals.*—When opening: Upper surface: Ranges between Violet Group 88A and Violet-Blue Group 90A. Lower surface: Ranges between Violet-Blue Group 89A and Violet-Blue Group 89B. Fully opened: Upper surface: Violet-Blue Group 90A, fades to Violet-Blue Group 90B. Lower surface: Ranges between Violet Group 88A and Violet-Blue Group 89C.

Bud:
*Shape.*—Obovate.
*Length.*—5 mm.
*Diameter.*—3 mm.
*Color.*—Violet-Blue Group 89B for over 90% of buds in calyx; calyx is colored Greyed-Purple Group 186B.

Calyx:
*Arrangement.*—5 sepals fused into a tube at 50% of the length; 3 upper sepals fused nearly at the tips; 2 lower sepals fused nearly at the tips.
*Height.*—5 mm.
*Diameter.*—3 mm.
*Shape.*—Tubular.
*Sepals.*—Shape: Elliptic with acute tip and crenate base. Size: Average 5 mm long; 1.5 mm wide. Margin: Entire. Texture: Grayish hairs; less than 0.2 mm long. Color: Immature: Upper surface: More greenish than Greyed-Purple Group 186B. Lower surface: Greyed-Purple Group 186B. Mature: Upper surface: Green Group 137B with edge of Greyed-Purple Group 186B. Lower surface: Green Group 137B with edge of Greyed-Purple Group 186B. Bracts: 2 bracts under each whorl of flowers; deltoid shape with apiculate tip; between Green Group 143A and Green Group 143B; densely covered with grayish-white hairs less than 0.1 mm long.
*Odor.*—Present in petals and sepals.

REPRODUCTIVE ORGANS

Stamens:
*Number.*—2.
*Filament length.*—4.1 mm and 3.1 mm.
*Anthers.*—Shape: Basifixed, elliptic. Length: 0.9 mm. Color: Greyed-Yellow Group 160C.
*Pollen.*—Color: Light grayed-yellow; too low amount to determine color. Amount: Very low.

Pistil:
*Number.*—One.
*Length.*—1 cm.
*Style.*—Length: 9 mm. Color: Violet-Blue Group 90B shading to Violet-Blue Group 91B at base.
*Stigma.*—Shape: Cleft (2 parted). Color: Violet-Blue Group 89B. Ovary color: Yellow-Green Group 144A.

Seeds and fruits: None.

Disease/pest resistance: No unusual susceptibility to diseases or pests has been noted to date.

Temperature tolerance: Tolerate to heat at least up to 30° C. and cool at least down to USDA Zone 5.

I claim:

1. A new and distinct variety of Salvia plant substantially as shown and described.

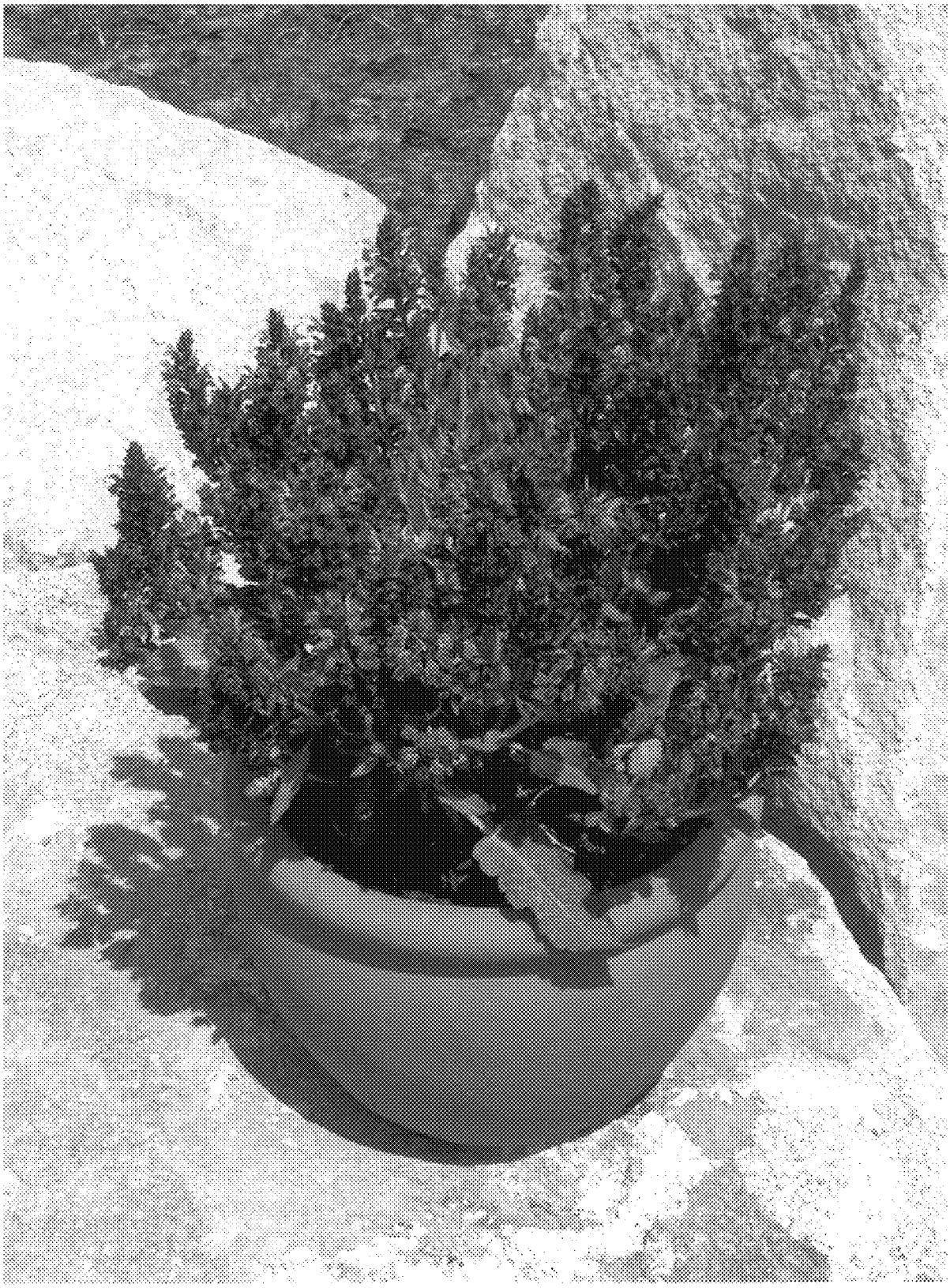

* * * * *